(12) United States Patent
Bi et al.

(10) Patent No.: US 9,157,846 B1
(45) Date of Patent: Oct. 13, 2015

(54) BOB FOR TESTING RHEOLOGY AND OVERCOMING THE WEISSENBERG EFFECT

(71) Applicants: Hongfeng Bi, Houston, TX (US); Joseph Bi, Houston, TX (US); Rebecca Bi, Houston, TX (US)

(72) Inventors: Hongfeng Bi, Houston, TX (US); Joseph Bi, Houston, TX (US); Rebecca Bi, Houston, TX (US)

( * ) Notice: Subject to any disclaimer, the term of this patent is extended or adjusted under 35 U.S.C. 154(b) by 363 days.

(21) Appl. No.: 13/731,863

(22) Filed: Dec. 31, 2012

(51) Int. Cl.
*G01N 11/14* (2006.01)

(52) U.S. Cl.
CPC .................................... *G01N 11/14* (2013.01)

(58) Field of Classification Search
CPC ..................................................... G01N 11/14
USPC ............ 73/54.28, 54.29, 54.31, 54.32, 54.33, 73/54.34, 54.35
See application file for complete search history.

(56) References Cited

U.S. PATENT DOCUMENTS

| | | | |
|---|---|---|---|
| 485,376 | A | 11/1892 | Fuller |
| 1,025,828 | A | 5/1912 | Paul |
| 2,492,884 | A | 12/1949 | Patermaster |
| 3,405,450 | A | 10/1968 | Peacock |
| 4,876,018 | A | 10/1989 | Karydas |
| 4,993,448 | A | 2/1991 | Karydas et al. |
| 5,365,777 | A * | 11/1994 | Layton .......................... 73/54.28 |
| 6,412,338 | B2 | 7/2002 | Boyle et al. |
| 7,287,416 | B1 * | 10/2007 | Bi ................................ 73/54.28 |
| 2003/0192366 | A1 | 10/2003 | Taylor |
| 2011/0198187 | A1 * | 8/2011 | Lukay et al. ................. 192/84.1 |

* cited by examiner

*Primary Examiner* — Hezron E Williams
*Assistant Examiner* — David Z Huang

(57) ABSTRACT

A hollow bob (20A) with a plurality of circumferentially spaced holes (30A). The hollow bob (20A) is attached to a bob shaft (10A) and is submerged in a test fluid (40A).

18 Claims, 3 Drawing Sheets

US 9,157,846 B1

BOB FOR TESTING RHEOLOGY AND OVERCOMING THE WEISSENBERG EFFECT

BACKGROUND

1. Field of Invention

Figure 1:
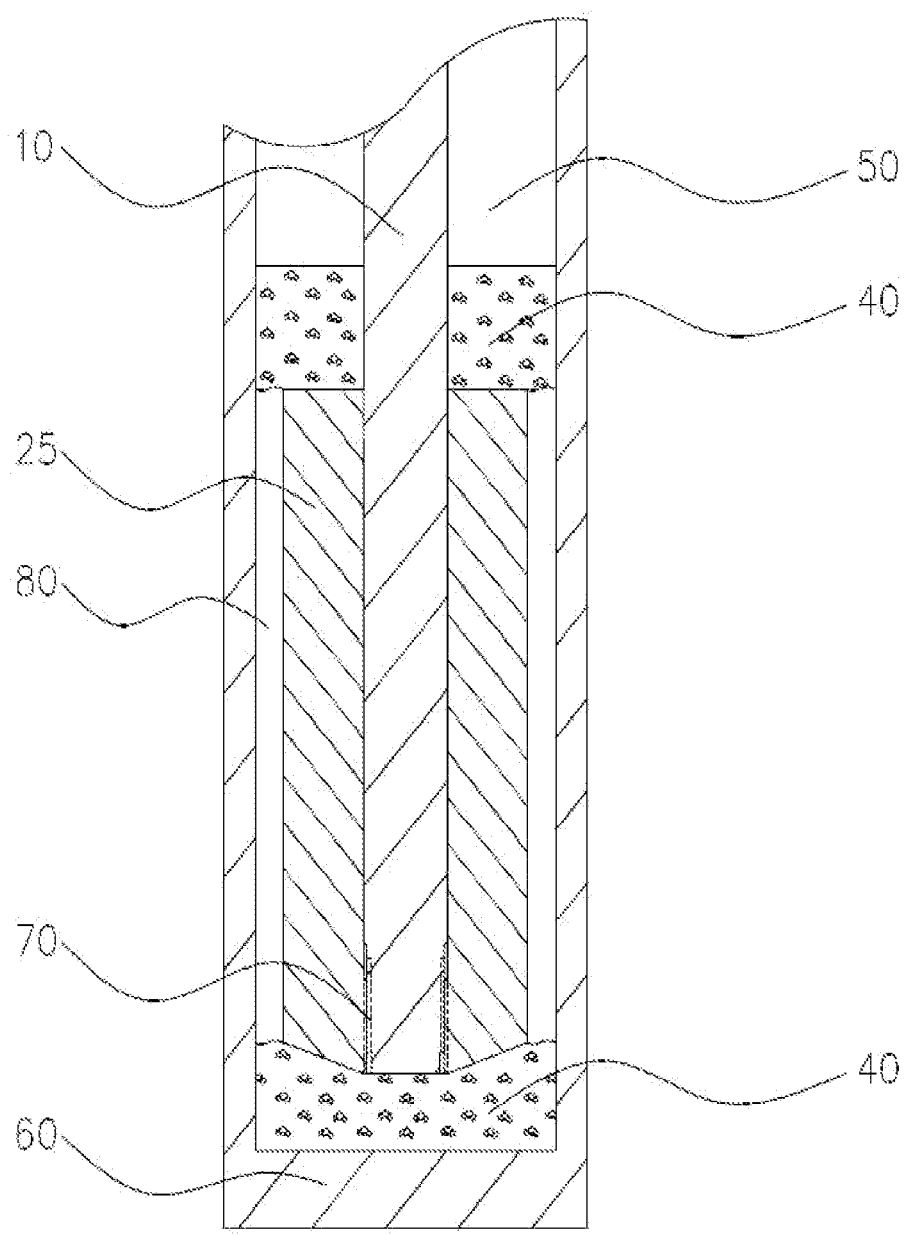

The present invention relates to using a bob with off-centered axial direction holes for testing the rheology of non-Newtonian fluids and overcoming the Weissenberg effect.

2. Description of Prior Art

The process of drilling wells, particularly in the petrochemical industry, has changed dramatically over the past few years, with much of that change having to do with the chemical makeup and rheological behavior of the fluids used to manage and operate the wells. The drilling process has become much less dependent on brute-force mechanical methods and turned instead to using chemistry to accomplish many of the necessary functions of drilling the well. This has necessitated a much greater understanding of the predicted viscoelastic behavior of chemical fluids, particularly those under down-hole conditions which can be extreme and changeable in ways that are difficult to anticipate.

Testing mechanisms for these fluids have also changed significantly, as the viscosity, temperature sensitivity, and rheological behavior of the tested fluids has diversified. This improved type of test equipment must be capable of measuring wider ranges of test fluid properties than in the past, with faster and more repeatable measurement response, while remaining as reliable, accurate, durable and easy to use as possible.

Another challenge pertains to testing non-Newtonian fluids, as these fluids commonly exhibit the "Weissenberg effect". The Weissenberg effect describes the tendency of a non-Newtonian fluid to climb up a rotating rod. If there is air or pressurization gas above the sample fluid, the Weissenberg effect also causes the sample fluid to climb out of the measurement range of a co-axial cylinder geometry rheometer, thus causing inaccurate measurement. Therefore, it would be desirable to provide a method for determining the rheology of non-Newtonian fluids without the detrimental impact of the Weissenberg effect.

U.S. Pat. No. 6,412,338 teaches a viscometer containing a bob with circumferentially spaced openings, but the design of the bob is intended for a measurement chamber filled with one type of homogenous fluid only. If there is gas above the sample fluid in the measurement chamber, a non-Newtonian sample would still climb out of the measurement gap between the coaxial bob and cup and thus the design provides no remedy to the problem of the Weissenberg effect. U.S. Pat. No. 6,412,338 would also suffer from measurement inaccuracy because the radial direction holes on the bob surface would cause non-uniform shear rates at the location of these holes and thus provide inaccurate results.

Therefore, it is an object of this invention to provide a bob configured for the rheological testing of non-Newtonian sample fluids with gas or empty space on top of tested sample fluid while overcoming the Weissenberg effect in any test environment.

SUMMARY

In a gas pressurized coaxial cylindrical geometry viscometer, the liquid sample in the cup would climb out of the measurement zone due to the Weissenberg effect. A hollow bob configured in accord with the present invention comprises a bob connecting to a bob shaft and with multiple axial direction holes from one end of the bob to the other. Providing axial direction holes inside the bob, arranged annularly around the center, would create a circulation path, thus refilling the gap in the measurement zone should the Weissenberg effect occur. In an open, atmospheric viscometer, axial direction holes are also provided inside of the bob, arranged annularly around the center, to counter the Weissenberg effect.

Also, because of the differential shearing at the bottom of the cup and the bob, the fluid is sheared more at the outside than inside, thus causing fluid to recirculate along the measurement zone and axial direction holes inside the bob, if the Weissenberg effect occurs.

DRAWING FIGURES

Figure 2:
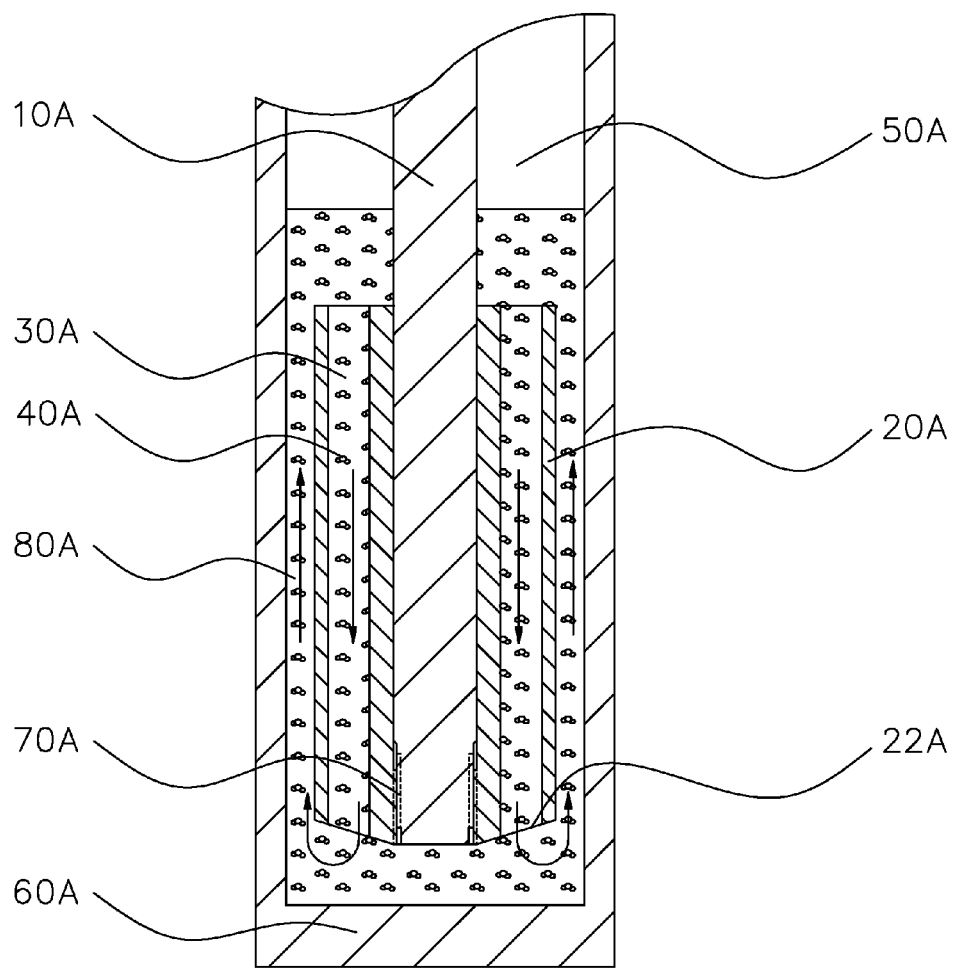
Figure 3:
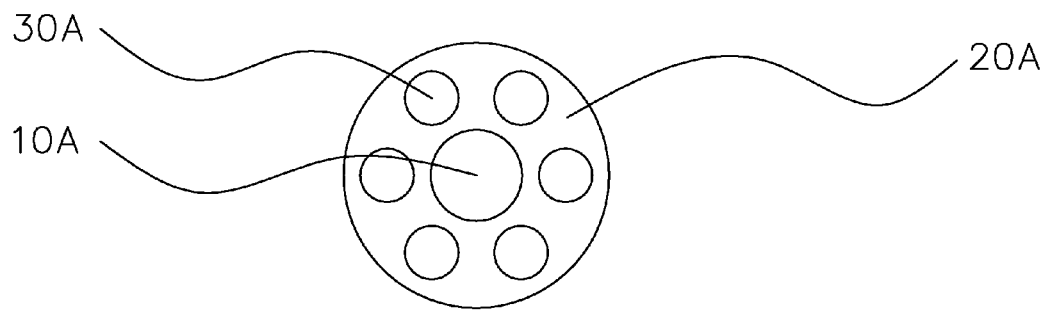
Figure 4:
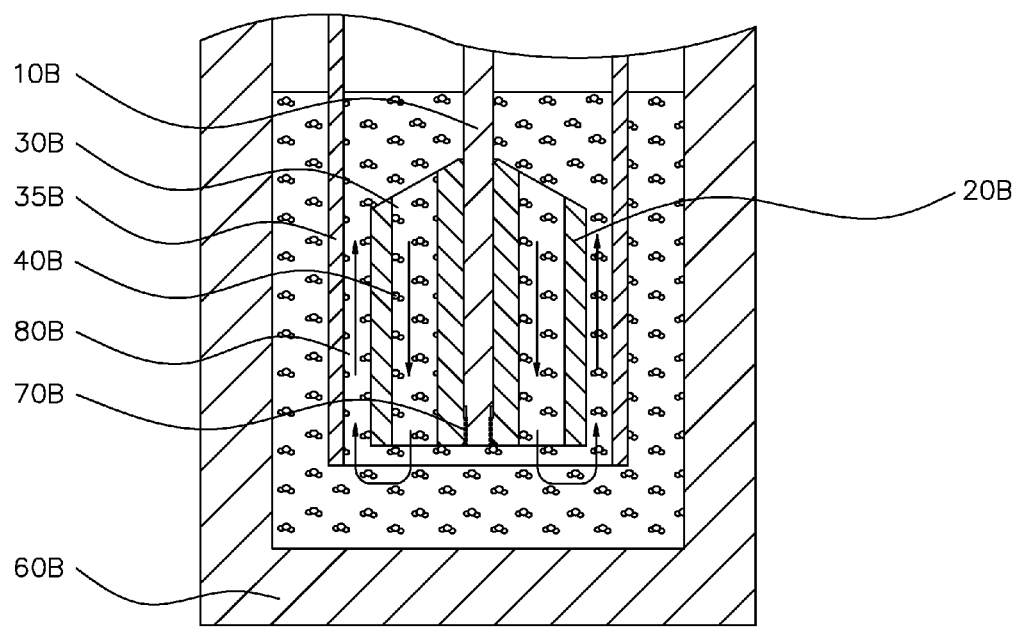
Figure 5:
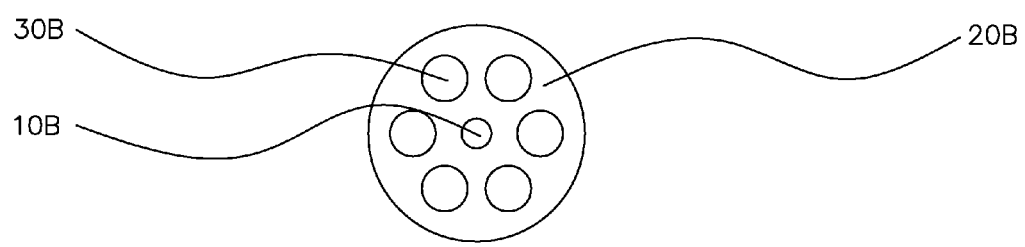

Other objects, features and advantages will be apparent from the following detailed description of preferred embodiments taken in conjunction with accompanying drawings in which:

FIG. 1 is a cross-section view of an embodiment without the axial direction holes, which illustrates the Weissenberg effect, FIG. 2 is a cross-section view of a preferred embodiment of the invention in a nitrogen-pressurized viscometer, FIG. 3 is a top-down view of a preferred embodiment of the invention, FIG. 4 is a cross-section view of a bob in an atmospheric viscometer and FIG. 5 is a top-down view of a bob in an atmospheric viscometer.

REFERENCE NUMERALS IN DRAWINGS 10 bob shaft
10A bob shaft
10B bob shaft
20A hollow bob
20B hollow bob
22A truncated cone
25 solid bob
30A holes
30B holes
35B sleeve
40 test fluid gel
40A test fluid gel
40B test fluid gel
50 pressurization media
50A pressurization media
60 sample cup
60A sample cup
60B sample cup
70 screw thread
70A screw thread
70B screw thread
80 gap
80A gap 80B gap Description—FIG. 1

FIG. 1 is a cross-section view of a cylindrically-shaped solid bob 25 attached to a bob shaft 10 via a screw thread 70. Solid bob 25 is submerged in a cylindrically-shaped sample cup 60 which is partially filled with a test fluid gel 40 and is being pressurized by a pressurization media 50, such as $N_2$ gas. There is an annular cylindrical gap 80 between solid bob 25 and sample cup 60.

Operation—FIG. 1

Assemble solid bob 25 by attaching it to bob shaft 10 via screw thread 70. Fill sample cup 60 with test fluid gel 40 till solid bob 25 is covered. Inject pressurization media 50 by any conventional means in order to pressurize sample cup 60. Rotate sample cup 60 at a constant speed to provide shear on test fluid gel 40 in such a way which satisfies test requirements. Test fluid gel 40 applies rotational torque on solid bob 25, due to fluid viscosity. This torque can be measured by any conventional means to back-calculate the viscosity of test fluid gel 40. However, the rotation of sample cup 60, applied to the non-Newtonian test fluid gel 40 would cause the Weissenberg effect to occur, and thus cause the fluid to climb out of the measurement zone gap 80.

Furthermore, because test fluid gel 40 possesses viscoelastic gel properties, it can stay at the top of solid bob 25 and not fall back to gap 80. The Weissenberg effect is most problematic when sample cup 60 is rotating at constant speed and is not much present when sample cup 60 is undergoing oscillatory movements.

Alternatively, sample cup 60 could be stationary and a torque is applied on solid bob 25, causing solid bob 25 to rotate. This torque is required to overcome the viscosity of test fluid gel 40 and can be measured by any conventional means. The Weissenberg effect will occur in this situation as well because test fluid gel 40 would climb along rotating solid bob 25 and out of measurement zone gap 80.

Description—FIG. 2 and FIG. 3

FIG. 2 shows a hollow bob 20A with a sample cup 60A. A plurality of discrete circumferentially spaced axial direction holes 30A, arranged annularly around the center, extend from one end of hollow bob 20A to the other. Hollow bob 20A is mainly in cylindrical shape with a truncated cone 22A bottom. Hollow bob 20A is attached to a rotatable bob shaft 10A via a screw thread 70A. Sample cup 60A is partially filled with a test fluid gel 40A and is being pressurized by a pressurization media 50A, such as $N_2$ gas. Test fluid gel 40A at least covers the top of hollow bob 20A. There is an annular cylindrical gap 80A between hollow bob 20A and sample cup 60A.

FIG. 3 shows hollow bob 20A from a top-down perspective which reveals the plurality of discrete circumferentially spaced axial direction holes 30A extending from one end of hollow bob 20A to the other. Bob shaft 10A is positioned in the center of hollow bob 20A.

Operation—FIG. 2 and FIG. 3

Assemble hollow bob 20A by attaching it to bob shaft 10A via screw thread 70A. Fill sample cup 60A with test fluid gel 40A until hollow bob 20A is submerged inside sample cup 60A. Inject pressurization media 50A by any conventional means in order to pressurize sample cup 60A. Rotate sample cup 60A at a constant speed to provide shear on test fluid gel 40A in such a way which satisfies test requirements. Test fluid gel 40A applies rotational torque on hollow bob 20A, due to fluid viscosity. This torque can be measured by any conventional means to back-calculate the viscosity of test fluid gel 40A. Due to the different shear applied on test fluid gel 40A at the bottom of sample cup 60A by virtue of the annularly-arranged holes 30A in hollow bob 20A, and truncated cone 22A at the bottom of hollow bob 20A, the rotation of sample cup 60A causes test fluid gel 40A to recirculate through the gap 80A, thus substantially reducing the Weissenberg effect and enabling greater test accuracy. Also, if test fluid gel 40A climbs out of measurement zone gap 80A, the hydraulic column pressure of test fluid gel 40A inside of holes 30A would generate a pressure imbalance between holes 30A and measurement zone gap 80A. This pressure imbalance also forces test fluid gel 40A to flow back to measurement zone gap 80A.

Description—FIG. 4 and FIG. 5

FIG. 4 shows a hollow bob 20B, a cylindrical shaped sleeve 35B and a sample cup 60B. A plurality of discrete circumferentially spaced axial direction holes 30B, arranged annularly around the center, extend from one end of hollow bob 20B to the other. Hollow bob 20B is attached to a rotatable bob shaft 10B via a screw thread 70B. Hollow bob 20B is submerged in sample cup 60B which is partially filled with a test fluid gel 40B. There is an annular cylindrical gap 80B between hollow bob 20B and sleeve 35B.

FIG. 5 shows hollow bob 20B from a top-down perspective which reveals the plurality of discrete circumferentially spaced axial direction holes 30B extending from one end of hollow bob 20B to the other. Bob shaft 10B is positioned in the center of hollow bob 20B.

Operation—FIG. 4 and FIG. 5

Assemble hollow bob 20B by attaching it to bob shaft 10B via screw thread 70B. Fill sample cup 60B with test fluid gel 40B until hollow bob 20B is submerged in sample cup 60B. Rotate sleeve 35B at a constant speed to provide shear on test fluid gel 40B in such a way which satisfies test requirements. Test fluid gel 40B applies rotational torque on hollow bob 20B, due to fluid viscosity. This torque can be measured by any conventional means to back-calculate the viscosity of test fluid gel 40B. Due to the different shear applied on test fluid gel 40B at the bottom of sample cup 60B by virtue of the annularly-arranged holes 30B in hollow bob 20B, the rotation of sleeve 35B causes test fluid gel 40B to recirculate through the gap 80B, thus substantially reducing the Weissenberg effect and enabling greater test accuracy. Also, if test fluid gel 40B climbs out of measurement zone gap 80B, the hydraulic column pressure of test fluid gel 40B inside of holes 30B would generate a pressure imbalance between holes 30B and measurement zone gap 80B. This pressure imbalance also forces test fluid gel 40B to flow back to measurement zone gap 80B.

RAMIFICATIONS

In FIG. 2, hollow bob 20A does not have to be completely cylindrical in shape. It could be a cone, a truncated cone, a cylinder with fins on the outside, or other geometrical shape.

In FIG. 2, hollow bob 20A can be attached to bob shaft 10A by any conventional means, such as a screw thread, set screw, or cotter pin.

In FIG. 2, the discrete holes in hollow bob 20A do not have to be cylindrical in shape. They could be rectangular, triangular, oblong, or other geometrical shape.

In FIG. 2, the discrete holes in hollow bob 20A could be any number or diameter required for different testing parameters.

In FIG. 2, the discrete holes in hollow bob 20A do not have to be the same size on both ends of the bob. They could be partially closed off at any point inside the bob.

In FIG. 2, the discrete holes in hollow bob 20A do not all have to be the same size or geometrical shape. They could vary in size and/or shape as required for different testing parameters.

In FIG. 2, screw thread 70A could also be located at the middle or top of hollow bob 20A as long as screw thread 70A can fix hollow bob 20A to bob shaft 10A. The length of bob shaft 10A can vary as well.

In FIG. 4, sleeve 35B could also be stationary and hollow bob 20B is driven to rotate.

In FIG. 2, pressurization media 50A could also be a vacuum or atmospheric air if sample boiling is not a problem or testing parameter is desired as such.

CONCLUSION, AND SCOPE

Accordingly, the reader will see that this invention can be used in combination with a viscometer for accurate, widely varied, and repeatable measurement tests of fluid rheology using a great variety of test fluids. The configuration of the hollow bob enables repeatable and reliable test operation using a broad selection of test types, methods and environments.

OBJECTS AND ADVANTAGES

From the description above, the advantage of my hollow bob becomes evident. Due to the plurality of discrete circumferentially spaced holes, annularly arranged around the center of the bob, the current invention provides a recirculation path, which reduces the tendency of more viscous fluids, such as gels or cross-linked fluids to exhibit the "Weissenberg effect", and this will result in enhanced accuracy of test results and the ability of the user to create more varied and specific test routines, utilizing various rotational speeds for the bob and more varied sample compositions than would be easily accomplished with a solid bob.

Further objects and advantages of my invention will become apparent from a consideration of the drawings and ensuing description.

The invention claimed is:

1. A viscometer comprised of:
   a) a bob which is substantially symmetrically shaped corresponding to an axis,
   b) a sleeve around said bob, said sleeve driven to rotate along said axis,
   c) a testing fluid covering said bob,
   d) a plurality of off-centered unobstructed holes inside of said bob along the direction of said axis, running from one end of said bob to the other end of said bob, wherein each of said plurality of off-centered unobstructed holes extends the entire length of the external wall of said bob,
   e) means to measure the torque applied on said bob.

2. A viscometer according to claim 1 further comprised of a space above said testing fluid.

3. A viscometer according to claim 2, wherein said space is filled with a pressurization gas.

4. A viscometer according to claim 2, wherein said space is filled with atmospheric air.

5. A viscometer according to claim 2, wherein said space is a vacuum.

6. A viscometer according to claim 1, wherein said bob has a cylindrical shape.

7. A viscometer according to claim 1, wherein said bob has a truncated cone shape.

8. A viscometer according to claim 1, wherein said off-centered unobstructed holes have a cylindrical shape.

9. A viscometer according to claim 1, wherein said off-centered unobstructed holes have an oblong shape.

10. A viscometer comprised of:
    a) a bob which is driven to rotate corresponding to an axis,
    b) a stationary sleeve around said bob,
    c) a testing fluid covering said bob,
    d) a plurality of off-centered unobstructed holes inside of said bob along the direction of said axis, running from one end of said bob to the other end of said bob, wherein each of said plurality of off-centered unobstructed holes extends the entire length of the external wall of said bob.
    e) means to measure the torque applied on said bob.

11. A viscometer according to claim 10 further comprised of a space above said testing fluid.

12. A viscometer according to claim 11, wherein said space is filled with a pressurization gas.

13. A viscometer according to claim 11, wherein said space is filled with atmospheric air.

14. A viscometer according to claim 11, wherein said space is a vacuum.

15. A viscometer according to claim 10, wherein said bob has a cylindrical shape.

16. A viscometer according to claim 10, wherein said bob has a truncated cone shape.

17. A viscometer according to claim 10, wherein said off-centered unobstructed holes have a cylindrical shape.

18. A viscometer according to claim 10, wherein said off-centered unobstructed holes have an oblong shape.

* * * * *